United States Patent [19]
Liu et al.

[11] Patent Number: 5,842,310
[45] Date of Patent: Dec. 1, 1998

[54] VESSEL FOR ECOLOGICAL PLANT TISSUE CULTURE ON A LARGE SCALE

[76] Inventors: Sijiu Liu; Wannan Xu, both of 262 Harvard St. Apt. #8, Cambridge, Mass. 02139

[21] Appl. No.: 827,442

[22] Filed: Mar. 27, 1997

[51] Int. Cl.[6] .................................................... C12M 3/00
[52] U.S. Cl. .................. 47/59; 435/304.1; 435/304.2; 47/62; 47/63; 47/65.5; 47/66.1
[58] Field of Search .............................. 47/62, 63, 65.5, 47/66.5, 79; 435/304.1, 304.2, 305.1, 305.2; 17/59, 62, 63, 65.5, 66.1

[56] References Cited

U.S. PATENT DOCUMENTS

| | | | |
|---|---|---|---|
| 4,908,315 | 3/1990 | Kertz | 435/240 |
| 5,088,231 | 2/1992 | Kertz | 47/1.01 |
| 5,119,588 | 6/1992 | Timmis et al. | 435/299 |
| 5,171,683 | 12/1992 | Kertz | 435/240 |
| 5,212,906 | 5/1993 | Noboru et al. | 47/62 |
| 5,426,889 | 6/1995 | Buora et al. | 47/79 |
| 5,525,505 | 6/1996 | Young et al. | 435/240 |

FOREIGN PATENT DOCUMENTS

| | | | |
|---|---|---|---|
| 87104410 | 2/1988 | China | C12N 5/00 |
| 2164535 | 3/1986 | United Kingdom . | |

OTHER PUBLICATIONS

Sijiu Liu et al. (1988) Plant tissue exposure Culture in Vitro Journal of Beijing Forestry University, vol. 10, No. 2 p. 107 (in chinese).

*Primary Examiner*—David A. Redding

[57] ABSTRACT

A new vessel for large scale plant tissue culture with a compartmentalized reservoir and corresponding media but without regular closure to close the vessel, so that the plant tissues cultured with the vessel are under a normal ecological air environment. Instead of the regular closure, a layer of sterile powder material is dusted on the top of the media and on a special circumferential fold on the wall of the vessel, until all the media, the fold, and the plant tissues are buried. Thus a continuous powder buried from wall to wall is formed against microbes from getting into the vessel. Since the normal ecological air environment provides a natural light, variable and normal humidity, air current, and enough $CO_2$, etc., the plantlets cultured from the new vessel harden themselves while they are gradually growing out of the powder layer, just like seedlings gradually growing out of soil in nature. The quality of the plantlets, in many aspects, is comparable to that of the nursery seedlings, in terms of hardiness and survival ability. Therefore, the traditional artificial hardening phase can be eliminated and the shelf and culture room area saved.

15 Claims, 9 Drawing Sheets

VESSEL FOR ECOLOGICAL PLANT TISSUE CULTURE ON A LARGE SCALE

BACKGROUND

1. Field of the Invention

This invention relates to plant tissue culture or plant micropropagation, especially to the vessel for a large scale plant tissue culture in a normal ecological air environment.

2. Description of Prior Art

This is a substitute application for our previous one which was allowed to go abandoned. The previous application was filed on Feb. 2, 1996 with the Ser. No. 08/595,764 and the title "Open culturing vessel for large scale plant micropropagation in vitro".

Plant tissue culture industry is severely limited by its high production cost compared to that of a nursery. The main reason for the high production cost is the over tenderness of the test tube plants that are too delicate to survive after being transplanted to the normal ecological air environment. In the traditional plant tissue culture, in order to protect the culture medium from contamination, people also enclose the plant tissues inside the closed container together with the wet medium on which the plant tissues are cultured. Therefore, it is man not the plants who should be responsible for the over tenderness. In fact all plants normally have their own means to resist the microbes and to cope with the ambient variables in nature.

The closure materials of tissue culture containers such as plastic film, paper, cotton, or the jar lid allow only a very limited amount of gas exchange, so that the conditions inside the containers are anti-ecology with extremely high humidity, without natural light, and air current, or insufficient $CO_2$, and too much ethylene and other accumulated harmful gases. Under such abnormal ecological conditions the plantlets are spoiled, disarmed, and of course disabled. Therefore, the conventional plant tissue culture must be supplemented by some additional procedures to harden the plantlets, such as tenting, misting, and shading them for weeks in the greenhouse after they are transferred out of the closed containers. Obviously, those procedures need more labor and facilities and increase the production cost. Even after passing through the hardening phase, the survival rate in most plant species is still not high enough. Many of them are well below 80 percent. Clearly, the problem of the traditional plant tissue culture originates from the anti-ecology way of culture.

In 1987 Sijiu Liu, Chunling Dai and Xin Shen disclosed a plant tissue exposure culture method in an abandoned Chinese patent application, titled "plant tissue exposure culture and equipment" No. 87104410. In 1988, the same inventors published a paper titled "plant tissue exposure culture in vitro" in the Journal of Beijing Forestry University, Vol. 10, No.2, June 1988, p.107–112. In contrast to the conventional closed way of tissue culture, those documents described an open way of plant tissue culture in vitro. The inventors also designed some special vessels for their described method.

Briefly, the vessel in the first prior art, is a beaker-like open mouth container with a side mouth for adding water to the container. A glass dish is suspended in the container above the water for containing the medium. Water supply during culture is done by a strip of gauze with one end buried in the medium and the other going through the gap between the container and the dish and finally soaked into the water. After inoculation, the plant tissues, the medium, and the gauze, are all covered with a layer of sterile powder coated with wax. The side mouth is covered with ordinary closure. The whole system allows the plant tissues inoculated to grow out of the powder layer but still keeps the medium, the gauze, and the water in aseptic condition.

Besides the container described above, other three ramifications were disclosed in the second prior art: a) with a perforated glass plate having a vertical handle in the center, b) with a glass ring; both the glass plate and the glass ring need to be wrapped by a piece of gauze with the excess part of the gauze tied up into a bundle and soaked into the water. The wrapped plate or ring is then put in the container above the water which is supported by three round protrusions from the inner wall. Those two ramifications can only receive the medium when cooling down near to semi-solid state because warm medium will leak through the gauze into water.

Embodiment c) of the second prior art is a container with a built-in plate above the water for containing medium. A pipe stands in the plate center. The strip of gauze whose one end is buried in the medium and the other going through the pipe and extending down into the water provides a path of water supply during culture (the gauze was not shown in the original figure). Embodiment d) is the same container as that in the first prior art, but has a segment of a big glass pipe to support the glass dish.

All four kinds of designs and methods described above to perform the exposure culture need a piece of gauze to form a path of water supply when the plant tissues are growing and consuming water in the medium. Gauze is not only a consumption item but also creates a complicated operation. To put the strip of gauze going through the gap between the container and the dish, or going through the pipe in the center is by no means an easy task in terms of efficiency of production. To wrap the glass ring or glass plate and tie up the excess part of the gauze into a bundle and soak into the water is even worse. That is the first problem of the prior art.

The second problem of the prior art is that the containers designed are only suitable for lab experiment. It is not suitable for large scale plant tissue culture or micropropagation industry.

Everyone knows that containers for lab use can not be simply enlarged in size for large scale industry. Although larger containers save labor and increase efficiency, the risk of their total contamination area will also increase.

The third problem of the prior art is the leakage of the powder into water from the gap mentioned. Since there has to be a gap or a pipe for the gauze to go through, the fine powder drops into the water along the wall very often. The problem not only looks unpleasant, but also causes partial exposure of the medium and contamination.

The fourth problem or disadvantage of the prior art is the side mouth. It occupies a space that decreases the shelf efficiency. It was designed for adding more water during culture, but the average culture period of 4–6 weeks, does not normally need additional water. On the other hand, the side mouth does add more production cost.

Finally, the fifth problem or disadvantage of the prior art is the higher cost of the powder material which tends to stick together and forms lumps.

Robert Ou Young disclosed in UK patent GB 2164535A a device for propagating seeds or plants comprising a reservoir vessel, a water supply vessel, and a seed and/or plant propagating container which supports the two vessels and receiving water from them through a siphon device for the germinating seeds/sprouts. Bruno Buora et al in U.S. Pat.

No. 5,426,889 also disclosed an automatic watering device for cultivation of plants in pots.

The above two patents are generally related to our present invention in form. But they are not suitable for culturing isolated plant tissues or explants on sterile medium. They can only work in a non-sterile condition. They do not comprise any special feature or element to prevent microbes from getting into the devices and contaminating the sterile medium.

In addition to the different use of the devices, the feature of double reservoirs in both of the above disclosures (the reservoir vessel and the water supply vessel in the first patent, the lower pot and inner tank in the second), is certainly not the same with our present invention.

Other related U.S. patents in the field of plant tissue culture did provide devices with special features or elements to protect the medium from contamination. However, all the devices work in a close way of culture and isolate the plant tissues and the resulting plantlets from the normal ambient during culture; thus, the over tenderness of the cultured plants is still inavoidable. In other words, those devices protect the plants at the expense of the health of the plants. This is absolutely not the feature and result of our present invention. The above related patents include the followings: U.S. Pat. No. 4,908,315 U.S. Pat. No. 5,088,231 U.S. Pat. No. 5,119,588 U.S. Pat. No. 5,171,683 U.S. Pat. No. 5,212,906 and U.S. Pat. No. 5,525,505.

OBJECTS OF INVENTION

Accordingly several objects of this invention are as follows:

1. It is our major object to provide a vessel for ecological plant tissue culture that allows the cultured plants to grow on a sterile culture medium without contamination, and that allows the cultured plants to grow under a normal ecological air environment to avoid the over tenderness; therefore, to result in extra healthy plants at low cost.
2. It is another object to provide a vessel for ecological plant tissue culture that eliminates the need of gauze or the like totally; therefore, the new vessel can save the gauze material and also labor used thereof by simplifying the operation procedure.
3. To provide a vessel for ecological plant tissue culture that can be enlarged for a large scale industry without increasing the risk of contamination.
4. To provide a vessel for ecological plant tissue culture that can eliminate powder leakage and avoid contamination therefrom.
5. To provide a vessel for ecological plant tissue culture that eliminates the side mouth so as to increase the shelf efficiency.
6. To provide a new powder material that eliminates the problem of clump formation and reduces the cost. Further objects and advantages will become apparent from consideration of the ensuing description and drawings.

DRAWING FIGURES

FIG. 6 is a plane view of the inner piece or medium-loading means; both FIG. 5 and FIG. 6 show a plurality of medium compartments, their extensions, and bottom holes from different directions.

REFERENCE NUMERALS IN DRAWINGS

10 Outer piece
12 Reservoir compartment
14 Stopper
16 Fold structure
18 Inner piece/Medium-loading means
19 Bottom hole
20 Extension
21 Opening
22 Medium compartment
23 Partition
24 Expansion
26 Medium
28 Plant tissue
30 Powder layer
32 Junction area
34 Plantlet
36 Pipe
37 Ordinary closure
38 Common bottom
40 Connection point
42 Handle
44 Solid reservoir
46 Film member
48 Independent reservoir
50 Culture tray for embodiment 4
52 Main tubing
54 Subtubing
56 Monitor
58 Wing of the monitor
60 Water level monitored
62 Clip means
64 Filter

GENERAL DESCRIPTION OF THE INVENTION

The vessel of an embodiment for example, comprises an outer piece which is compartmentalized into a plurality of reservoir compartments for containing liquid, and an inner piece or medium-loading means which is compartmentalized into a corresponding number of medium compartments for loading medium. On the inner wall of the outer piece there is a circumferential belt-like platform or fold structure on which the inner piece with medium is suspended.

Each medium compartment of the medium-loading means has a tube-like extension from the bottom leading to a reservoir compartment below. A portion of the medium filled in the extension becomes semi-solid and forms a path of liquid supply from the reservoir to the rest of medium. Thus no gauze nor other similar material is needed to form the path. The medium itself does the job. Besides, each reservoir compartment supplements liquid to only one medium compartment respectively. If by any chance, one of the medium compartments gets contaminated, the contamination will not spread to the others via reservoir. These features are the most important advantages of the present invention.

A corresponding plurality of stoppers releasably stop the fast flow of medium via the extensions into the reservoirs when the medium is in liquid state before and during autoclaving. However, the stoppers are not a necessity of the vessel, because if a warm medium is added to the vessel at a temperature near to set, the medium becomes semi-solid in the extension immediately and acts as a plug to stop the fast liquid flow but still allows the permeation and water supply. If a liquid medium with solid support material is used in the vessel, the solid support material will have the same functions as the semi-solid medium.

After inoculation, a layer of sterile fine sandy powder material is dusted over the sterile medium and the fold structure untill all the partitions of the medium compartments and a substantial height of the plant tissues inoculated are buried together with the medium and the fold structure. The powder with particle diameter 0.35–1.5 mm is made of hydrophobic material, such as plastic, either homogenous or heterogeneous. The powder material can be a mixture of different hydrophobic particles or a mixture with only one kind of particle. The powder material is sterilized by irradiation to eliminate the problem of clump formation.

The particle size of the prior art and the standard high-temperature method of sterilization tend to cause the clump formation.

The powder layer is actually a flexible closure of culture vessel. With this layer, all the inside part of the vessel is covered and protected from direct contact with the contaminators and therefore is kept aseptic. Because of the deposit of the powder particles on the fold structure, there will be no chance to form any gap between the powder layer and the wall. And because the particles of the powder are mobile and always ready to move, any gap in the powder layer caused by the tissue growth will be filled up instantly by the moving particles. On the other hand, since the powder layer covers rather than seals the vessel, the plant tissues inoculated are still allowed to grow out of the vessel through the layer freely to get the normal ecological air environment, and therefore to harden themselves gradually while growing. This is exactly the way that seedlings gradually germinated from the soil normally do in the nature. Besides, the powder material prevents microbes but not oxygen from getting into the layer, plant tissues buried under the layer can still grow normally.

The normal ecological air environment provides natural light, air current, normal and variable humidity, sufficient $CO_2$ and very little ethylene or other harmful micro gases. Therefore, the plantlets cultured from the vessel are comparable to those from traditional nursery, in terms of hardness and survival ability. Thus the hardening phase, one of the most costly phases in the traditional plant tissue culture, can be eliminated.

Since the ecological culture vessel is designed to be used in ordinary greenhouse instead of the more expensive culture room and is used only in the last subculture of the commercial production, (multiplication phase or root-induction phase), the new vessel can save ⅘ culture room area, if the plant species has a multiplication rate of 5. Ordinary the last subculture of the plant tissues occupies ⅘ area of the total culture room used.

The higher multiplication rate saves culture area. The culture room area (A) saved can be expressed as $A=(m-1)/m$. Here m represents the multiplication rate. For some easy rooting species, using the vessel in the last subculture of multiplication phase can also save ⅘ skilled labor, the most expensive labor who transfer plant tissues in the hood.

The ecological culture vessel is designed substantially larger than that used in lab in the prior art. Therefore, it is ideal for large scale plant tissue culture industry. In terms of culture area per vessel, our new vessel can be as large as ten times more than the conventional one, yet the risk of contamination still remains low.

Our objects can be accomplished by designing the vessel with two pieces as the example described above, or with only one piece; with a liquid reservoir or with a solid one; with a built-in reservoir or with a separate one. The details will be further described in the following embodiments.

DESCRIPTION OF THE EMBODIMENTS

Now referring to the figures we describe the major embodiments of the present invention.

Embodiment 1

The Back & Forth Type

Figure 1:
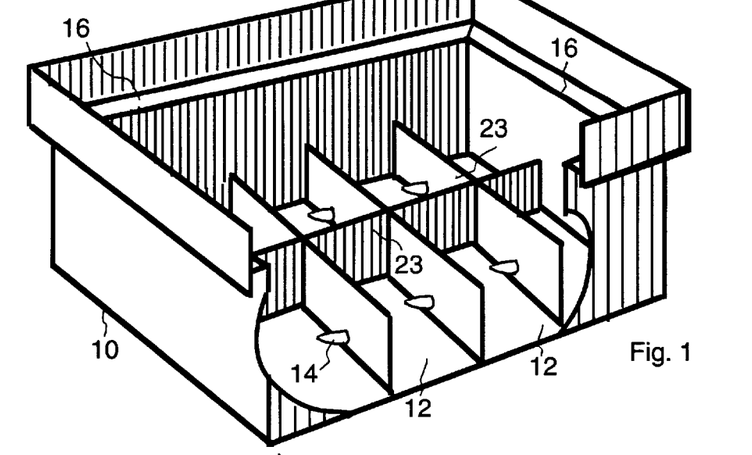
FIG. 1 is an exploded perspective view of the outer piece of the embodiment 1 which is a two-piece structure.
Figure 2:
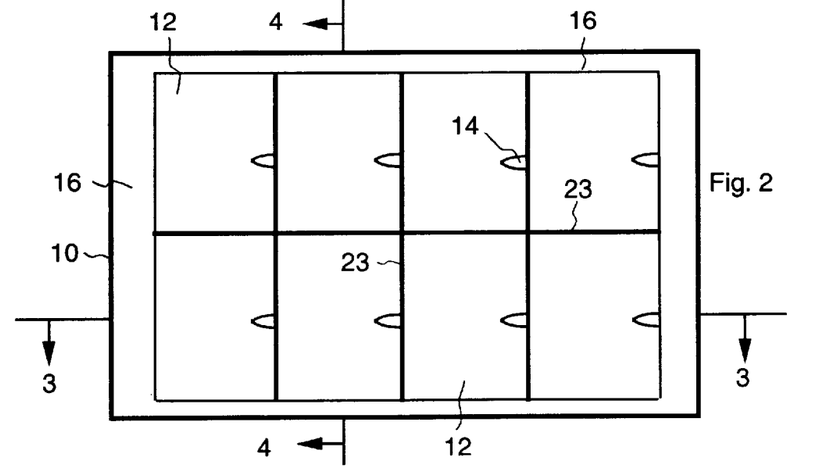
FIG. 2 is a plane view of the same piece of FIG. 1.

This type is a two-piece structure with one piece being pushed back & forth in the other to controll water supply. FIG. 1 shows the outer piece 10 of the vessel and how it is compartmentalized into reservoir compartments 12. The stoppers 14 can be seen as some protrusions on the wall. The most important feature of the vessel is the circumferential fold structure 16. On the outer piece is a inside circumferential fold structure 16 in a form of platform in FIG. 1. The platforms at two ends are wider than those at the sides as shown in FIG. 2, so that there will be enough room for the inner piece to be pushed back & forth without leaving a gap.

Figure 3:
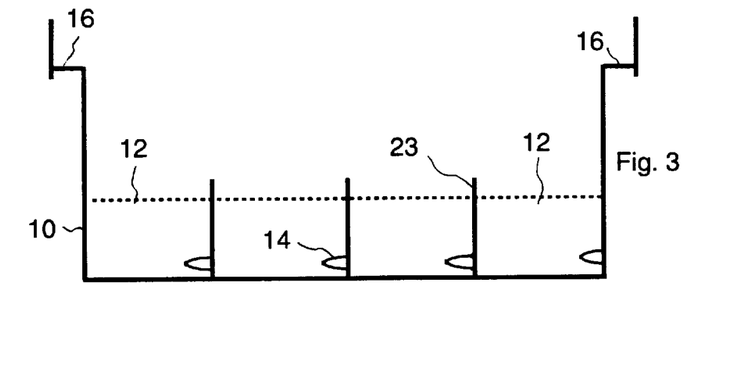
FIG. 3 is a section view of the same piece of FIG. 2 from the section line 3—3.
Figure 4:
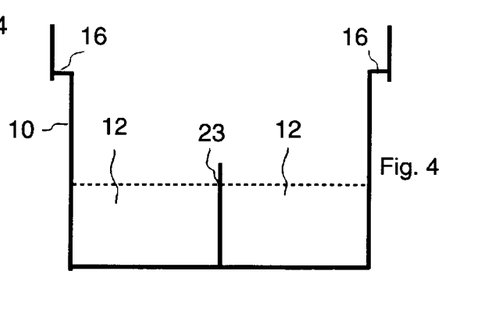
FIG. 4 is a section view of the same piece of FIG. 2 from the section line 4—4.

From section line 3—3, a longitudinal section view can be seen in FIG. 3, showing the reservoir compartments 12 with water stored. From the section line 4—4, a transverse section view of the outer piece 10 can be seen in FIG. 4.

Figure 5:
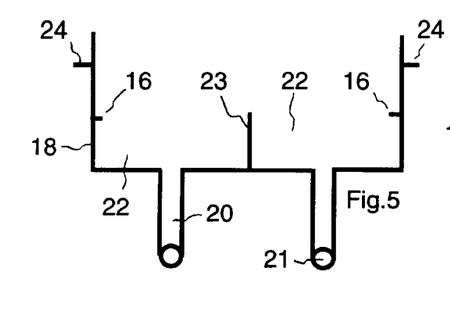
FIG. 5 is a transverse section view of the vessel of the embodiment 1.
Figure 6:
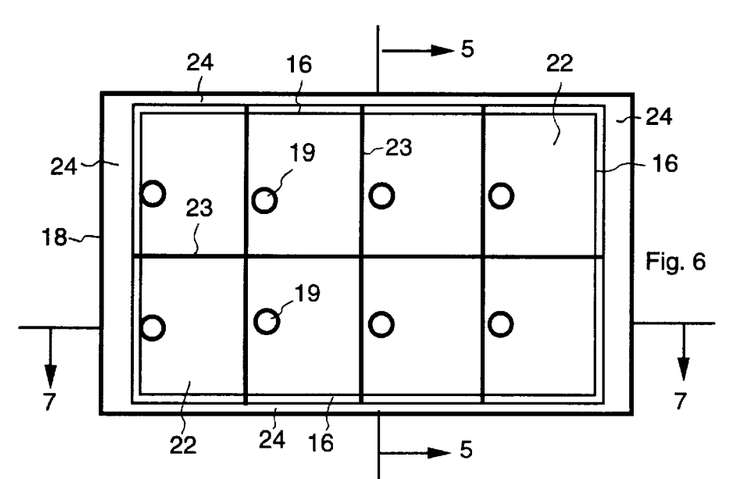

A transverse section view of the inner piece 18 (FIG. 5), the second piece of the two-piece structure shows the extensions 20 of the medium compartments 22 and circumferential fold structure 16. FIG. 6 is a top plane view of the inner piece, showing how it is compartmentalized with partitions 23 into medium compartments 22 for containing medium. FIG. 6 also illustrating the bottom holes 19, which is the inlets of the extensions 20, and the expansions 24 which are used for suspending the inner piece on the platforms.

Figure 7:
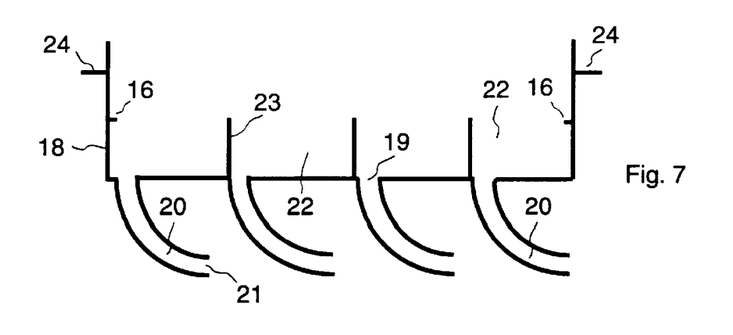
FIG. 7 is a longitudinal section view of FIG. 6 from the section line 7—7 showing the extension of the medium compartment being an arc tubes.

A longitudinal section view of the inner piece 18 (FIG. 7) from the section line 7—7 in FIG. 6, shows the extensions 20 as an arc tubes from the medium compartments down to the reservoir compartments.

Figure 8:
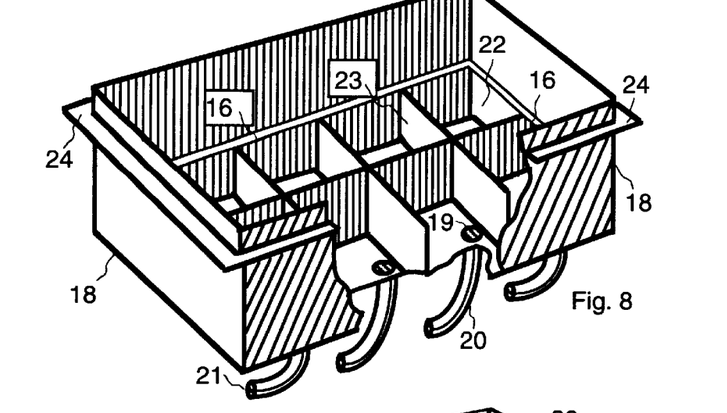
FIG. 8 is an exploded perspective view of the inner piece or medium-loading means.
Figure 9:
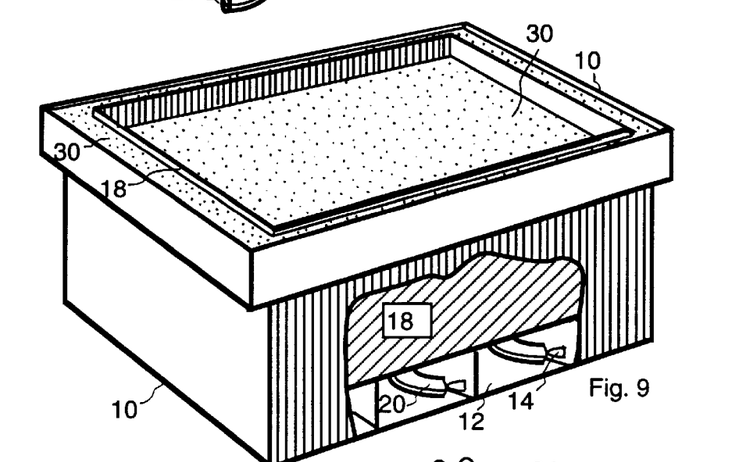
FIG. 9 is an exploded perspective view of the whole vessel of the invention, showing that the inner piece has been put inside the outer piece and covered by the powder material.
Figure 10:
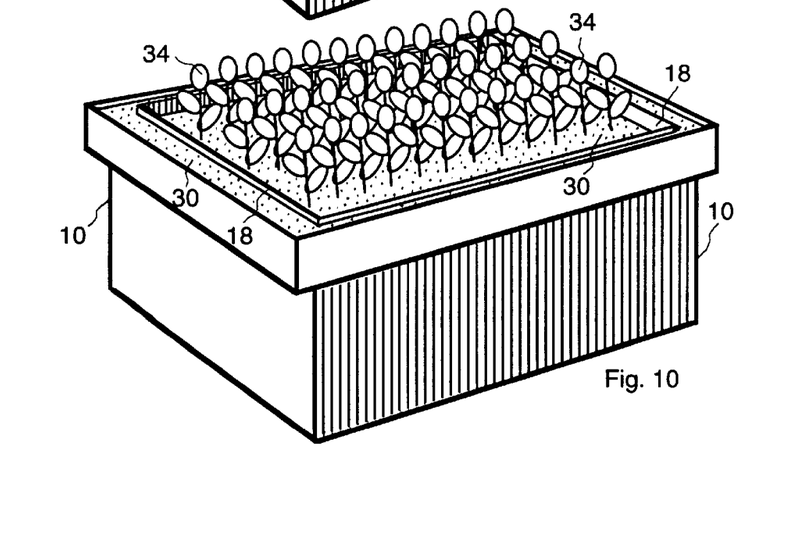
FIG. 10 is a perspective view of the whole vessel, showing the plantlets that have grown out of the layer of powder while the medium and all the inside parts are still protected from contamination.

An exploded perspective view of the inner piece (FIG. 8), illustrats in three dimensions of the whole vessel in which the inner piece 18 is already suspended. In order to show both the extensions 20 and the stoppers 14, the outer piece's wall has been exploded from the other side compared to FIG. 8. The layer of powder material covers not only the medium but also the junction area 32 of the two pieces, so that the inside of the vessel can remain in aseptic conditions (FIG. 9), and the plantlets 34 can grow out of the vessel through the powder layer and reach the ambient without destroying the aseptic condition (FIG. 10).

Figures 11, 12:
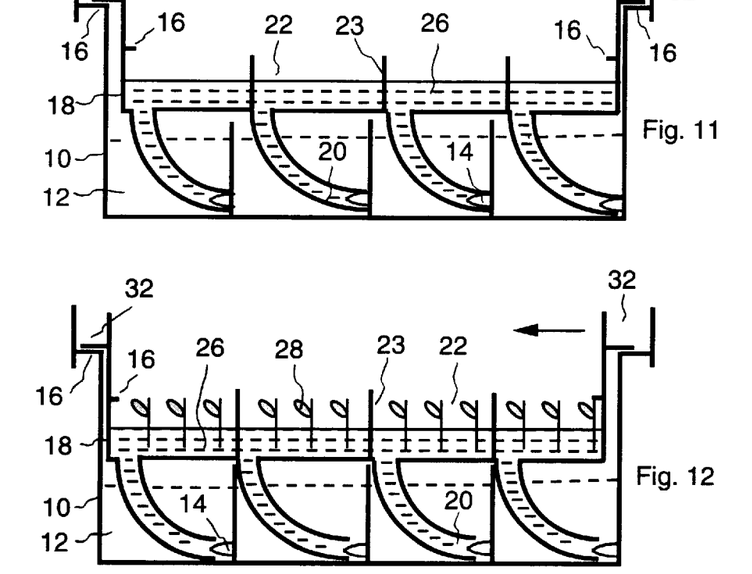
FIG. 11 and FIG. 12 are the longitudinal section views of the vessel showing how the extensions are plugged by the stoppers. Note the arrow directions.
Figure 13:
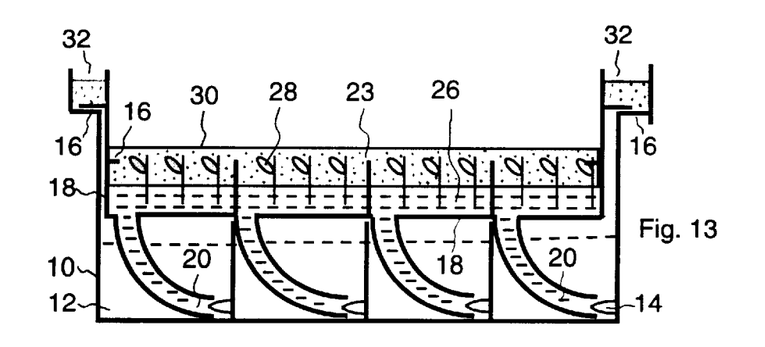
FIG. 13 shows how the medium and the plant tissues are covered by the powder. The junction area of the two pieces is also covered to ensure the aseptic condition inside the vessel.

FIGS. 11–13 show circumferential fold structure 16 on the outer piece 10 and inner piece 18 of the vessel 10.

The mechanism of closing and releasing of the extensions is shown in FIG. 11 and FIG. 12. The newly prepared warm medium or the medium during autoclaving is in liquid state. It becomes semi-solid only after cooling. Therefore, the openings 21 of the extensions 20 should be plugged by the stoppers 14 to avoid fast flow of medium into reservoir, if the medium is loaded into and autoclaved together with the vessel. But they should be released after cooling to allow slow permeation of water supply. To do this, give the inner piece 18 a simple push with a pair of forceps, from the left to the right (indicated by the arrows in the FIG. 11). Before inoculation, the inner piece should be pushed back (see the arrow in FIG. 12) to open the openings. Thereafter the inner piece position will not change and the openings 21 keep open to ensure water supply during the entire culture time (FIG. 13).

Figure 14A:
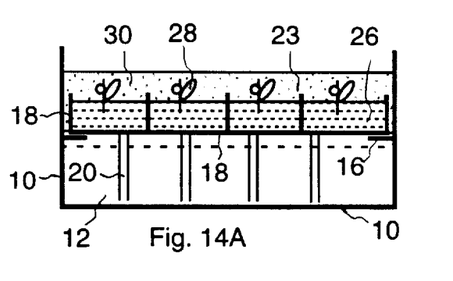
FIGS. 14A and B are two ramifications of the embodiment 1, with a two-piece structure but without relative movement of the two pieces.
Figure 14B:
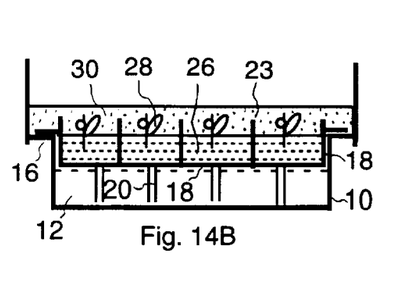

However, the above closing and releasing mechanism of the extensions is not the only way to solve the contradiction of fast flow and slow permeation. Two ramifications illustrated in FIG. 14A and FIG. 14B provide a even simpler solution. Instead of autoclaving the medium together with the vessel, autoclave them separately. The vessel with the liquid loaded is autoclaved and allowed to cool first, then the medium is autoclaved separately and poured into the vessel in the hood when the medium temperature is near to set. In this way, the medium will set immediately in the extensions without fast flowing.

The advantage of these ramifications is the simpler structure of the vessel, in which the relative movement of back & forth is no longer needed. The space for the movement and the stopper means are saved. As FIG. 14 indicated, the extensions are all straight, and the openings 21 are closer to the bottom, because the stopper means are eliminated.

Since the medium doesn't have to be autoclaved together with the vessel, the medium-loading means can be made shorter than the embodiment 1, and the medium level can be put above or below the level of the fold structure as indicated by FIG. 14A and FIG. 14B.

Embodiment 2

Up & Down Type

Figure 15:
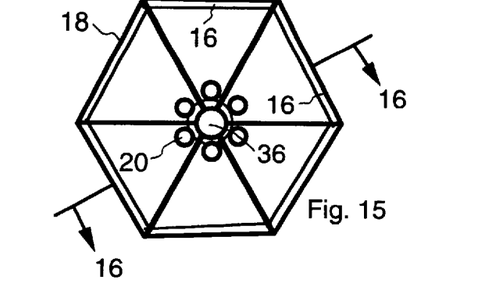
FIG. 15 is a top plane view of the embodiment 2 which is a one-piece structure.

This embodiment is a one-piece structure with an up & down moveable common bottom to control water supply. Instead of a separate medium-loading means, there is a built-in one in the vessel. The embodiment is typically shown in FIGS. 15–19. FIG. 15 is a top plane view from which only the built-in medium-loading means 18 can be seen. It is compartmentalized into a plurality of medium compartments 22, each with an extension 20. The embodiment further has a pipe 36 in the center which is covered by an ordinary closure 37 after adding water. The details are shown in FIG. 16 through the section line 16—16, all parts in this embodiment are inseparable.

There is also a plurality of reservoir compartments 12 each has its own bottom and own wall which is not shared by the adjacent compartments. Therefore, the reservoir compartments are basically isolated from one another. However, all of their central ends are connected or fixed to a second or common bottom 38, and their distal ends connected to the wall of the vessel with the connection points 40 (see FIG. 16–FIG. 18).

Figure 16:
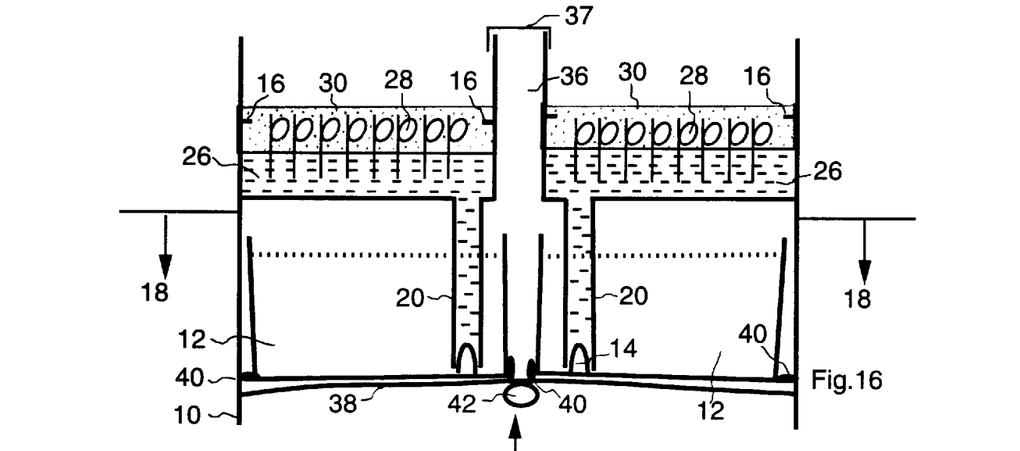
FIG. 16 is a longitudinal section view of FIG. 15 from the section line 16—16, showing the central pipe, the medium compartments and their extensions. The figure also shows the reservoir compartments and stoppers which have plugged the extensions.
Figure 17:
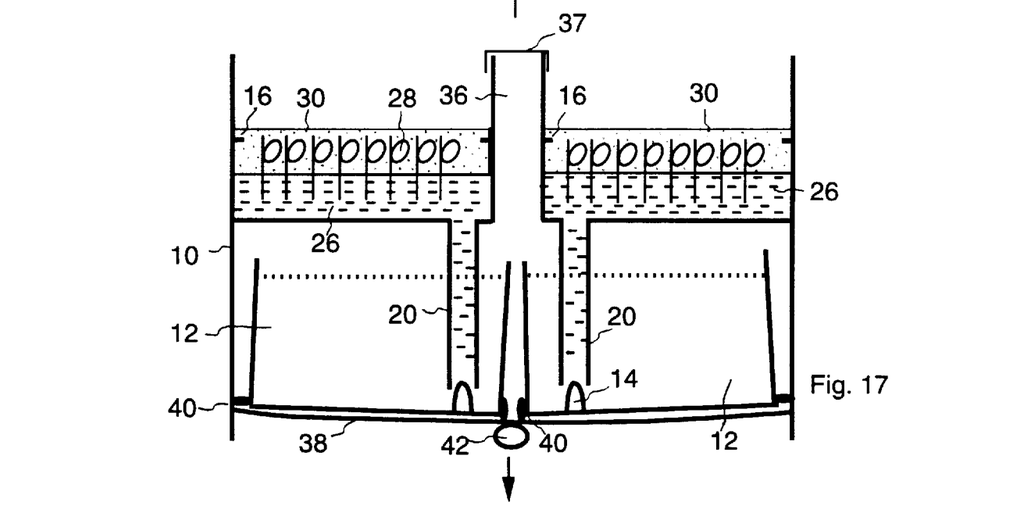
FIG. 17 is the same section view with FIG. 16, but the extensions have been unplugged. Note that the concave bottom has changed into the convex bottom and the moving directions of the stoppers indicated by the arrows.
Figure 18:
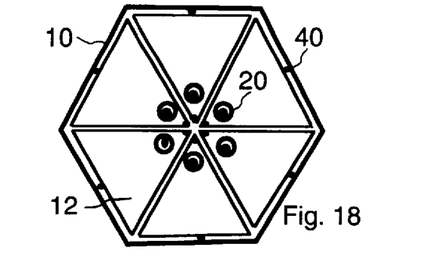
FIG. 18 is a transverse section view of FIGS. 16 and 17 from the section line of 18—18 in FIG. 16 showing the isolated reservoir compartments and the extensions.
Figure 19:
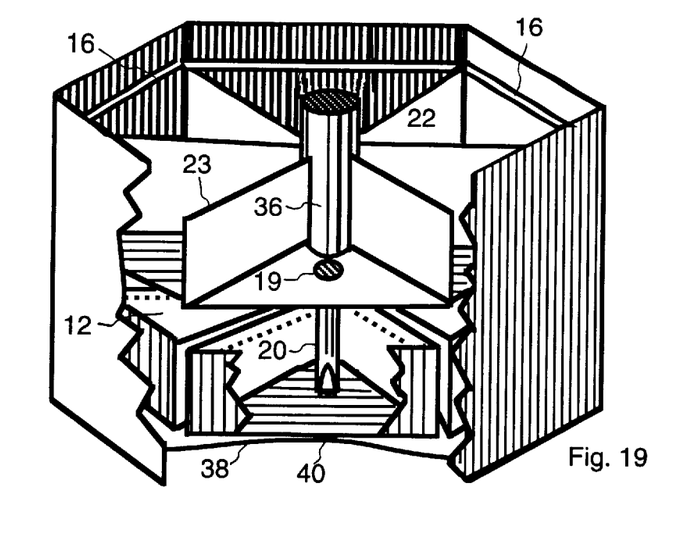
FIG. 19 is an exploded perspective view of the whole embodiment 2.

The common bottom 38 shown in FIG. 16 and FIG. 17 is either in a concave or a convex shape which can be changed by pushing up or pulling down from outside handle 42. The concave shape (FIG. 16) pushes all the reservoir compartments 12 and their stoppers 14 going up a distance just enough to plug up the openings 21; while the convex shape (FIG. 17) pulls down the stoppers to open the extensions 20 and allows liquid supply from the reservoirs to the medium 26. The above connection manner of the reservoir compartments gives the common bottom 38 a limited flexibility for the change. FIG. 18 from the section line 18—18 in FIG. 16, illustrats a transverse section view of the connection manner. FIG. 19 shows all the perspective details of the embodiment.

Figure 20:
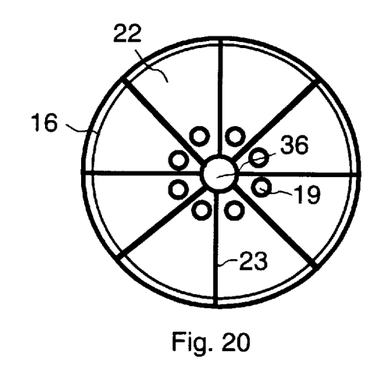
FIG. 20 is a ramification of the embodiment 2 with round outline.
Figure 21:
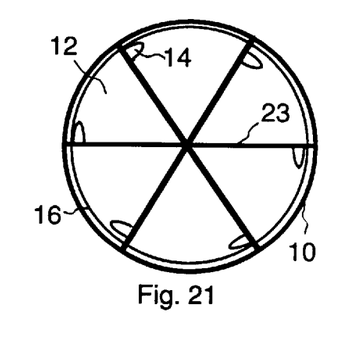
FIG. 21 is a ramification of the embodiment 1 with round outline.

This up & down movement can also be eliminated by similar structure like the ramifications in FIG. 14, if the medium is autoclaved separately. There are still other ramifications for the embodiment 1 and 2. FIG. 20 and FIG. 21 are new ramifications for the embodiments whose outlines are round in contrast to being rectangular.

Embodiment 3

Solid Reservoir Type

Instead of liquid reservoir seen in the prior art and in the embodiment 1 and 2 of the present invention, a solid reservoir is used in this embodiment. The solid reservoir is a complex of water and water-absorbing solid material 44, such as vermiculite, sands, or perlite. It can retain a great deal of liquid like water but does not shrink much after removal of the water, so that the medium loaded on it will not sink down with the consumption of water.

Figure 22:
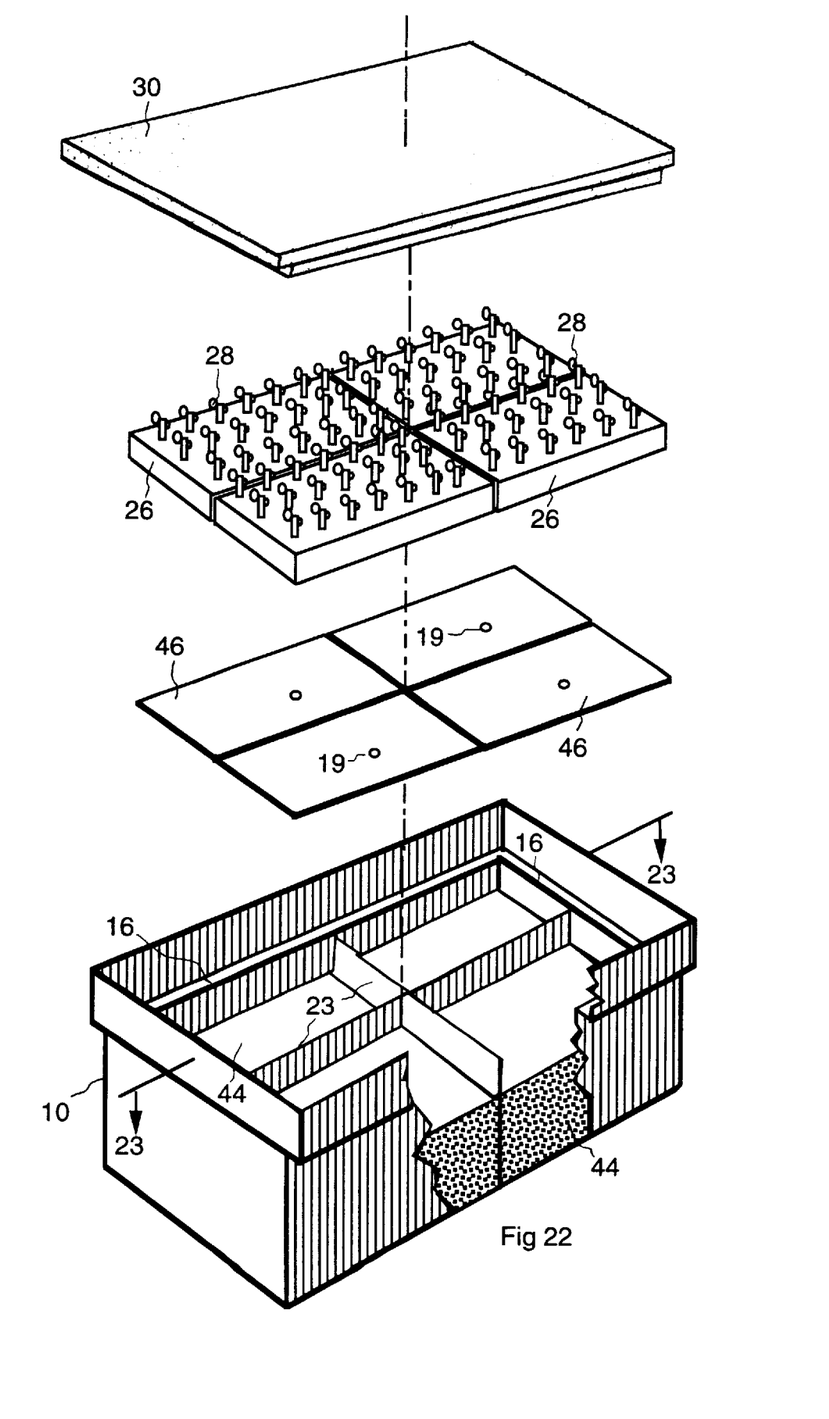
FIG. 22 is an exploded view of the embodiment 3, illustrating the solid reservoir, and the film member on it, etc.

The vessel used in this embodiment is similar to the outer piece of the embodiment 1. The lower part of the vessel is compartmentalized by partitions 23 into a plurality of compartments for containing the solid reservoir 44 at the bottom. The medium 26 is contained in the same compartment on the top of the solid reservoir (see FIG. 22 and FIG. 23). The total amount of both should be below the top level of the partitions 23. In order to avoid too much medium mixed into the solid reservoir, a thin plate or film member 46 which is fit to the compartment, is placed in between the solid reservoir and the medium. The medium is in fact loaded on the film member. It is therefore, actually a simplified medium-loading means. It may has one or more holes like other medium-loading means.

When the separately autoclaved warm medium 26 is poured into the cool, preautoclaved vessel which is already filled with the solid reservoir 44 and placed the film member 46, a portion of the medium penetrates into and sets in the solid reservoir through the hole or the edge of the film member. This portion of semi-solid medium itself forms a path of water supply by direct contact with the solid reservoir (see FIG. 23).

Figure 23:
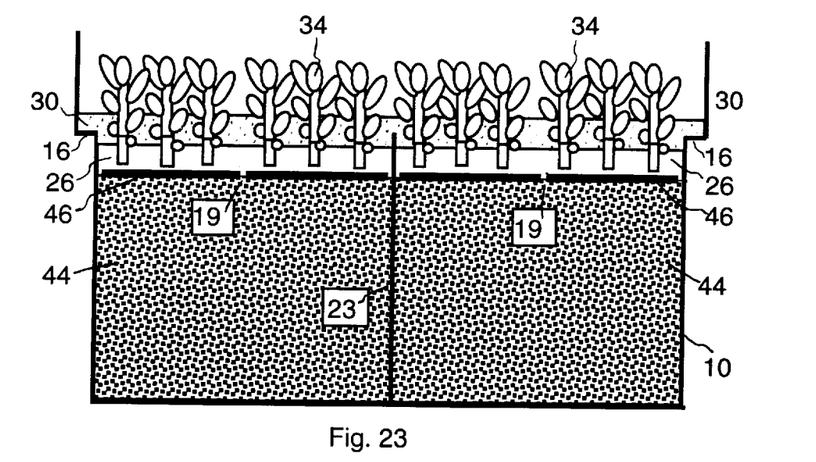
FIG. 23 is a section view of FIG. 22 from the section line 23, showing the details of the fold structure, and the plant tissues having grown out of the powder layer.

At the level of the partition's top 23, the wall of the vessel has a circumferential fold structure 16, on which and also on the semi-solid medium 26, a layer of sterile powder material 30 is dusted and deposited (FIG. 23). Because gravity exerts a greater pressure of the powder particles on the fold structure than on the vertical wall, the fold structure provides a wall to wall powder barrier against microbes from getting into the vessel and contamination along the inner surface of the vessel wall. Plant tissues growing out of the powder layer will not break the continuation of the powder barrier because of the mobility of the moving powder particles.

In order to avoid contamination spread from one compartment to another, it is important to control the medium level poured not over the top of the partitions and the fold structure (FIG. 23).

The thickness of the powder layer enough to protect the medium is similar to that of the other embodiments, in which at least the partition tops, the fold structures, and substantial height of the plant tissues inoculated are buried under the powder layer.

Figure 24:
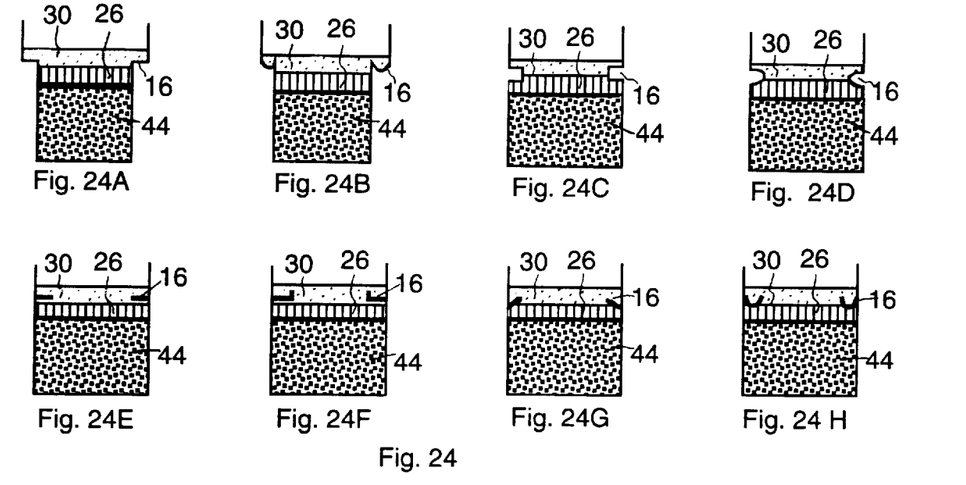
FIGS. 24A–H show a variety of the fold structures and the relative position of the medium to the fold structure.

There is a variety of types of the fold structure, which are slightly different from one another, but functionally the same (see FIG. 24). The outline of the vessel in the embodiments can be rectangular, square, round or other shapes.

In this embodiment the layer of medium in the vessel is no longer separated from the reservoir by an air space, as seen in the prior art. Therefore the vessel of this embodiment is the simplest one among others. Neither an intermediary material like gauze strip nor a complicated siphon mechanism described in the prior art of Robert Ou Young (UK Patent GB 2 164535A) is needed. This embodiment also has the simplest operation procedures.

Embodiment 4

Drip Irrigation Type

In this embodiment the water supply to medium is provided by a drip irrigation system from a separate reservoir. This system comprises an independent reservoir 48, a plurality of culture trays 50, a tubing system including a main tubing 52 and subtubing 54, with which liquid is distributed to the culture trays (see FIG. 25).

Figures 25, 26, 27:
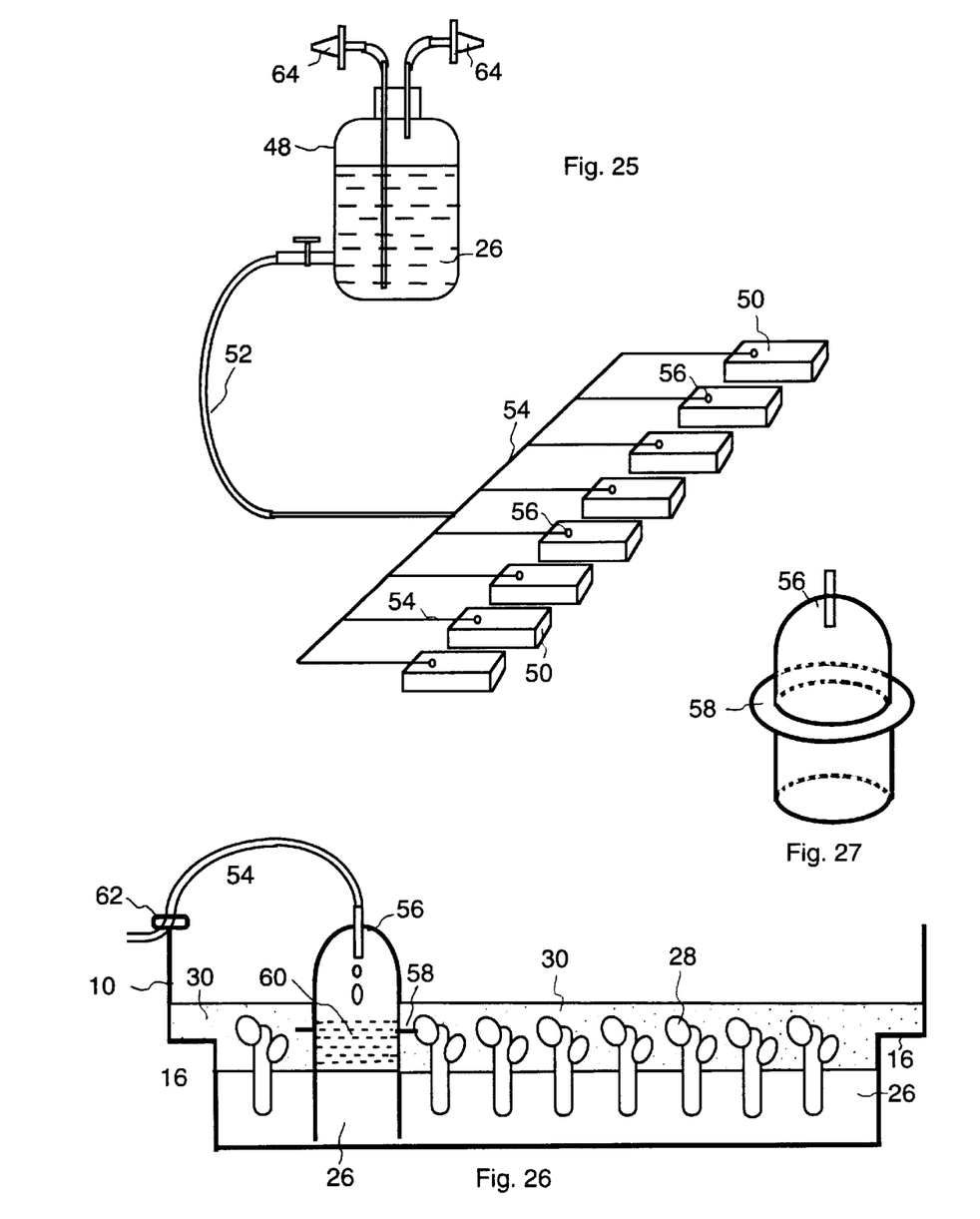
FIG. 25 is that of the embodiment 4 showing the independent reservoir, the tubing, and the culture trays.
FIG. 26 is a section view of the culture tray used in the embodiment 4, showing the tray with the fold structure, and the monitor.
FIG. 27 is a perspective view of the monitor.

In order to avoid excess or deficient water supply and to watch the level of dripping water, the end of the tubing system is connected to a transparent monitor means 56 which is pressed deeply into the medium in the tray 50 before dusting the sterile powder layer 30. A peripheral fold structure or wing 58 on the monitor 56 is designed to be buried in the powder layer when the powder is dusted on it (FIG. 26 and FIG. 27). The function of the wing 58 is to prevent the microbes from getting into the medium along the outer surface of the monitor.

The water level 60 dripped in the monitor can be seen through the transparent monitor 56 and adjusted from the reservoir during tissue culture. A clip means 62 is used to hold the sub-tubing 54 and the monitor 56 in position. Filter 64 is used to keep the reservoir aseptic and working normally.

The culture tray used in this embodiment also has at least one fold structure which, together with the medium, are covered and protected by the powder material. But there is no space for a built-in reservoir in the tray, therefore, the tray is much shorter. The shorter the tray is, the more racks can be built in each culture shelf, so that the more culture space can be saved. This type of embodiment has another advantage over the other types: it provides an easy way to manipulate the condition of the medium, such as adjusting pH value by adding new chemicals, changing hormone ratios by mixing new or existing chemicals in the water supply, etc. The manipulation of medium can even be more thorough if liquid medium with solid support is used in the vessel.

Although the description above contains many specificities, these should not be construed as limiting the scope of the invention, but merely provides illustrations of some of the presently preferred embodiments of this invention. The scope of the invention should be determined by the appended claims and their equivalents, rather than by the examples given.

Operative Advantages of the Invention

To use the vessel in the following procedures can greatly benefit the large scale plant micropropagation industry.

A. The Benefits Originate from the Quality of the Plantlets

In contrast with traditional closed way of tissue culture, the plantlets from the new culture vessel harden themselves in the normal ecological air environment, while they are steadily growing out of the powder layer. This hardening process is just like the seedlings steadily growing out of the soil in nature. The quality of the plantlets from the new vessel is, in many aspects, comparable to the normal greenhouse plantlets, especially the hardness and the survival ability. Therefore, the traditional hardening phase can be eliminated and the shelf and culture room area saved. This benefit is especially obvious for the following two tissue culture procedures.

B. Using the Vessel in Root-Induction Phase

For the difficult-to-root species, the vessel can be used in the root-induction phase in greenhouse instead of in culture room. That can save ⅘ (or 80%) culture room area (if the plant species has a multiplication rate of 5, the same below). This procedure does not require to build more greenhouse area, because this greenhouse area is normally used for the hardening phase any way. After the root-induction phase, the plantlets have already hardened themselves and are ready to be transferred to the cones or other commercial arrangement for sale. The hardening phase therefore is no longer needed. With this procedure, only ⅕ of the culture room area is needed for producing the stock explants in the conventional containers for the next circle of production.

C. Using the Vessel in the Last Subculture of Multiplication Phase

For the easy-to-root plant species, the vessel can be used in the last subculture of the multiplication phase in greenhouse. When the multiplication phase is finished, 5 times more hardened shoots can be picked as cuttings and be rooted in non-aseptic condition in greenhouse.

With this procedure, the amount of the stock explants needed for the next circle is ⅕ of the amount of the last subculture of the multiplication phase, which is again ⅕ of the amount of the root-induction phase. In other words, the culture room area needed for maintaining the production circle is only ⅕×⅕=1/25. Suppose the difficult-to-root and easy-to-root species are equal in number in the industry, the average culture room area needed is (⅕+1/25)/2=(6/25)/2= 12%. Apparently, this is a great advantage in reducing the production cost.

However, the amount of labor saving is even a greater advantage. Using the vessel in the second procedure, the amount of labor required for transferring the explants at the hood, the most expensive labor in the industry, is also only ⅕ (or 20%) of the conventional procedure, because the cutting and rooting process is not done at the hood at all.

D. Size Effect and Operative Efficiency of the Invention

Besides the procedural advantages of the vessel described above, there is still one other benefit of the present invention. It is the size effect. As every one knows that the larger the culture container, the higher the operative efficiency. However, it is also true that the larger the container the higher the risk of the contamination area. That is why the industry now is still using individual small containers. The vessel of the present invention, on the other hand, can be manufactured substantially larger, because compartmentalization of the culture medium and the reservoir greatly reduces the risk of contamination.

We claim:

1. A vessel for plant tissue culture comprising a sterile reservoir, a layer of sterile medium with plant tissues, and a layer of sterile powder material positioned on top of said medium to protect said medium from contamination, said vessel further comprising:

a) a fold structure on a circumferential and vertical wall of said vessel at the level of the layer of said powder material, said fold structure being an inwardly extending surface connected to said wall or a folding of said wall, said fold structure having a horizontal or inclined orientation relative to said vertical wall and a flat or curved shape, said powder material is deposited on said fold structure and on said sterile medium so as to form a continuous barrier for preventing microbes from contaminating the interior of said vessel; and b) a medium loading means for holding said sterile medium positioned below the level of said fold structure and comprising at least one medium compartment which has on it's bottom at least one inlet in flow communication with liquid contained within said reservoir, said medium extending from the compartment through said inlet to said reservoir so as to provide a permeation path for said liquid contained within said reservoir.

2. The vessel of claim 1 further comprising an additional fold structure.

3. The vessel of claim 1 wherein said fold structure is a sharply reduced waist of said vessel.

4. The vessel of claim 1 wherein said medium-loading-means having at least one medium compartment which is supported by said fold structure and fit in said vessel, the amount of medium that can be loaded being determined by the capacity of said medium compartment.

5. The vessel of claim 1 wherein said medium-loading-means having at least one medium compartment which is built on the wall above said reservoir compartment, the amount of medium that can be loaded being determined by the capacity of said medium compartment.

6. The vessel of claim 1 wherein said medium-loading-means comprising a thin plate or a film member which is supported by a solid reservoir, the maximum amount of medium that can be loaded being determined by a space between said film member and said fold structure.

7. The vessel of claim 1 wherein said inlet is an arc tube which is an extension of said medium compartment, said arc tube being releasably plugged by a relative movement of a stopper means on a wall of said reservoir compartment.

8. The vessel of claim 1 wherein said inlet is a straight tube which is an extension of said medium compartment, said tube being releasably plugged by a relative movement of a stopper means on a bottom of said reservoir compartment.

9. The vessel of claim 1 wherein said inlet is a bottom hole of a thin plate or film member, water supply being controlled by a predetermined size of said bottom hole.

10. The vessel of claim 1 wherein said inlet is a predetermined gap between a thin plate or film member and a wall of said medium compartment, water supply being controlled by a predetermined size of said gap.

11. The vessel of claim 1 wherein said reservoir contains a complex of liquid and liquid-absorbing solid material.

12. The vessel of claim 1 wherein said medium is semi-solid.

13. The vessel of claim 1 wherein said medium is liquid with sandy solid material.

14. The vessel of claim 1 wherein said powder material is a mixture of hydrophobic particles.

15. The vessel of claim 14 wherein said powder material is sterilized by the method selected from the group consisting of autoclaving and irradiation.

\* \* \* \* \*